US012583912B2

(12) United States Patent (10) Patent No.: US 12,583,912 B2
Takahashi et al. (45) Date of Patent: Mar. 24, 2026

(54) FLAVIVIRUS CROSS NEUTRALIZING ANTIBODY AND PHARMACEUTICAL COMPOSITION

(71) Applicant: Japan As Represented By Director General of National Institute of Infectious Diseases, Tokyo (JP)

(72) Inventors: Yoshimasa Takahashi, Tokyo (JP); Arnone Nithichanon, Tokyo (JP); Takayuki Matsumura, Tokyo (JP); Ryosuke Suzuki, Tokyo (JP); Chang-Kweng Lim, Tokyo (JP); Ganjana Lertmemongkolchai, Tokyo (JP)

(73) Assignee: JAPAN INSTITUTE FOR HEALTH SECURITY, Tokyo (JP)

( * ) Notice: Subject to any disclaimer, the term of this patent is extended or adjusted under 35 U.S.C. 154(b) by 848 days.

(21) Appl. No.: 17/801,075

(22) PCT Filed: Feb. 4, 2021

(86) PCT No.: PCT/JP2021/004022
§ 371 (c)(1),
(2) Date: Aug. 19, 2022

(87) PCT Pub. No.: WO2021/166654
PCT Pub. Date: Aug. 26, 2021

(65) Prior Publication Data
US 2023/0086835 A1 Mar. 23, 2023

(30) Foreign Application Priority Data
Feb. 20, 2020 (JP) ................................. 2020-026736

(51) Int. Cl.
*C07K 16/10* (2006.01)
*A61K 39/00* (2006.01)
*A61P 31/14* (2006.01)

(52) U.S. Cl.
CPC .......... *C07K 16/1081* (2013.01); *A61P 31/14* (2018.01); *A61K 2039/507* (2013.01); *C07K 2317/565* (2013.01); *C07K 2317/567* (2013.01)

(58) Field of Classification Search
CPC .................................................... A61P 31/14
See application file for complete search history.

(56) References Cited

U.S. PATENT DOCUMENTS

| | | |
|---|---|---|
| 2015/0328303 A1 | 11/2015 | De Silva et al. |
| 2016/0024189 A1 | 1/2016 | Marasco |
| 2018/0251531 A1 | 9/2018 | Marasco |
| 2020/0062830 A1 | 2/2020 | Marasco |

FOREIGN PATENT DOCUMENTS

| | | |
|---|---|---|
| JP | 2019-54796 A | 4/2019 |
| WO | 2017/212291 A1 | 12/2017 |
| WO | 2018/010789 A1 | 1/2018 |
| WO | 2018/187799 A1 | 10/2018 |

OTHER PUBLICATIONS

Almagro et al., Front. Immunol. 2018; 8:1751 (Year: 2018).*
Rudikoff et al., Proc. Nat'l Acad. Sci. USA, 79:1979-83 (1982) (Year: 1982).*
Brown et al., J. Immunol., 156(9):3285-91 (1996) (Year: 1996).*
Marvin et al., Biochemistry, 42(23):7077-7083 (2003) (Year: 2003).*
Chiu et al., Antibodies, 8(55):1-80. (2019) (Year: 2019).*
Davide F. Robbiani et al., "Recurrent Potent Human Neutralizing Antibodies to Zika Virus in Brazil and Mexico", Cell, 2017, vol. 169, pp. 597-609, e1-e7 (25 pages).
Extended European Search Report dated Feb. 26, 2024, issued in European Application No. 21757741.0.
Jiaqi Wang et al., "A Human Bi-specific Antibody against Zika Virus with High Therapeutic Potential", Cell, 2017, vol. 171, pp. 229-241 (29 pages).
International Search Report dated Apr. 13, 2021, issued in International Application No. PCT/JP2021/004022.
Gubler DJ et al., "Flaviviruses", In Fields virology (Fifth edition), 2007, Section II: Specific Virus Families, Chapter 34, pp. 1153-1252 (51 pages).
W. E. Brandt et al., "Infection Enhancement of Dengue Type 2 Virus in the U-937 Human Monocyte Cell Line by Antibodies to Flavivirus Cross-Reactive Determinants", Infection and Immunity, Jun. 1982, vol. 36, No. 3, pp. 1036-1041 (6 pages).
Halstead et al., "Dengue Viruses and Mononuclear Phagocytes", The Journal of Experimental Medicine, 1977, vol. 146, pp. 201-217 (17 pages).
Halstead et al., "Heterogeneity of Infection Enhancement of Dengue 2 Strains By Monoclonal Antibodies", The Journal of Immunology, 1984, vol. 132, No. 3, pp. 1529-1532 (5 pages).

* cited by examiner

Primary Examiner — Meera Natarajan
Assistant Examiner — Francesca Edgingtongiordano
(74) Attorney, Agent, or Firm — Sughrue Mion, PLLC

(57) ABSTRACT

Provided is a flavivirus cross neutralizing antibody which has an excellent ability to control infection with suppressed ADE. This is a flavivirus cross neutralizing antibody that specifically binds to domains of E protein of flavivirus and thereby has an ability to control infection with at least two viruses included in the flavivirus. The domains of E protein include a plurality of domains including domain III. The flavivirus includes, for example, Zika virus, dengue virus types 1-4, and Japanese encephalitis virus.

6 Claims, 2 Drawing Sheets
Specification includes a Sequence Listing.

[Fig. 1]
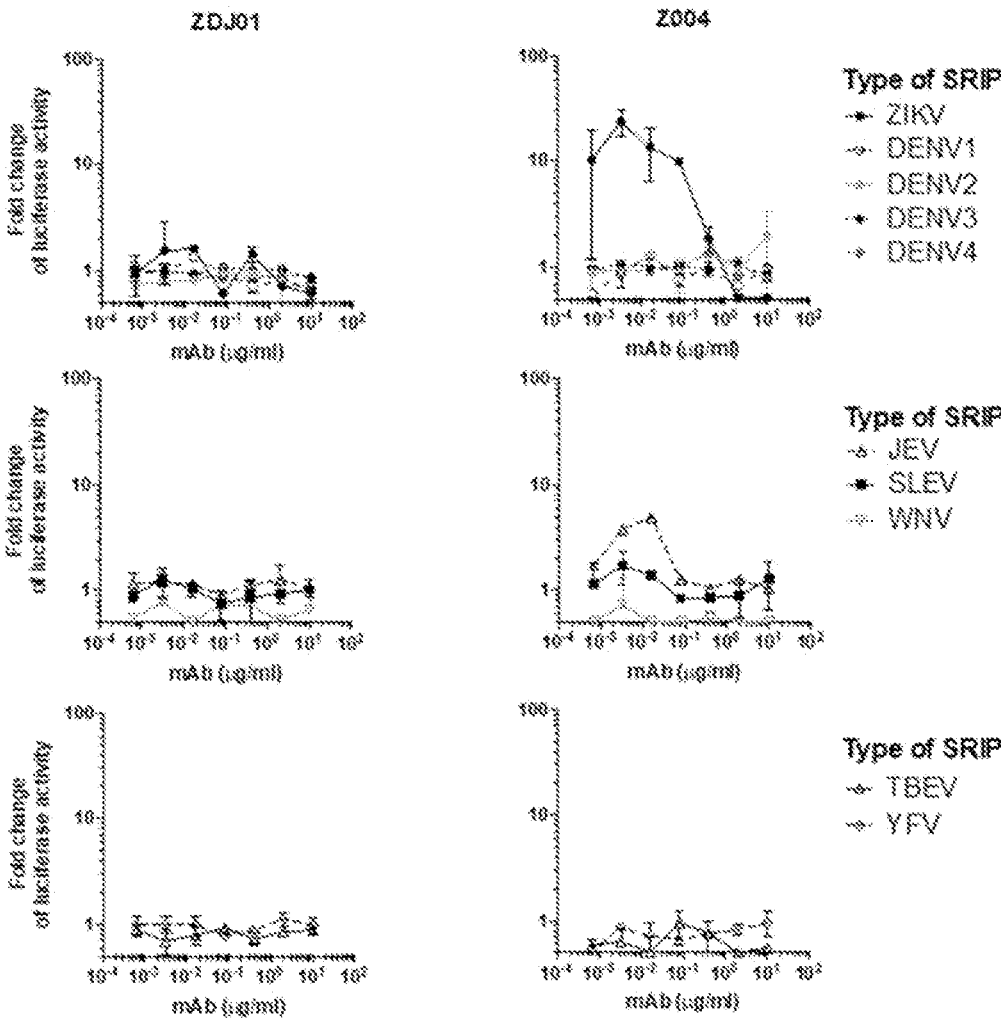

[Fig. 2]
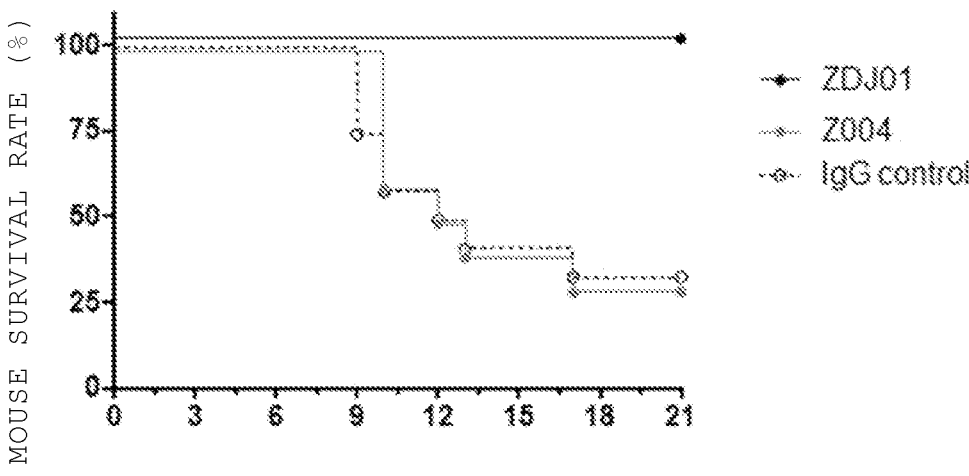

SEQUENCE LISTING

<160> NUMBER OF SEQ ID NOS: 15

<210> SEQ ID NO 1
<211> LENGTH: 129
<212> TYPE: PRT
<213> ORGANISM: Homo sapiens

<400> SEQUENCE: 1

```
Gln Met Gln Leu Val Gln Ser Gly Pro Glu Gly Lys Lys Pro Gly Thr
1               5                   10                  15

Ser Val Lys Val Ser Cys Lys Ala Ser Gly Phe Thr Phe Ser Arg Thr
            20                  25                  30

Thr Met Gln Trp Val Arg Gln Ala Pro Gly Gln Arg Leu Glu Trp Ile
        35                  40                  45

Gly Trp Ile Val Ile Gly Thr Gly Ser Thr Lys Tyr Ser Gln Asn Phe
    50                  55                  60

Gln Glu Arg Val Thr Phe Ser Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asn Pro Thr Thr Val Phe Gly Val Val Thr Pro Asp Tyr Tyr
            100                 105                 110

Tyr Tyr Pro Met Glu Val Trp Gly Gln Gly Thr Thr Val Thr Val Ser
        115                 120                 125

Ser
```

```
<210> SEQ ID NO 2
<211> LENGTH: 110
<212> TYPE: PRT
<213> ORGANISM: Homo sapiens

<400> SEQUENCE: 2

Gln Ser Val Leu Thr Gln Pro Pro Ser Ala Ser Gly Thr Pro Gly Gln
1               5                   10                  15

Arg Val Ala Ile Ser Cys Ser Gly Gly Asn Ser Asn Ile Gly Ser Asn
            20                  25                  30

Phe Val Tyr Trp Tyr Gln His Pro Pro Gly Thr Ala Pro Lys Leu Leu
        35                  40                  45

Ile Phe Arg Asn Asp Gln Arg Pro Ser Gly Val Pro Asp Arg Phe Ser
        50                  55                  60

Gly Ser Lys Ser Gly Thr Ser Ala Ser Leu Ala Val Ser Gly Leu Arg
65                  70                  75                  80

Thr Glu Asp Glu Ala Asp Tyr Phe Cys Ala Val Trp Asp Asp Thr Leu
                85                  90                  95

Arg Val Trp Val Phe Gly Gly Gly Thr Lys Leu Thr Val Leu
            100                 105                 110

<210> SEQ ID NO 3
<211> LENGTH: 8
<212> TYPE: PRT
<213> ORGANISM: Homo sapiens

<400> SEQUENCE: 3

Gly Phe Thr Phe Ser Arg Thr Thr
1               5

<210> SEQ ID NO 4
<211> LENGTH: 8
<212> TYPE: PRT
<213> ORGANISM: Homo sapiens

<400> SEQUENCE: 4

Ile Val Ile Gly Thr Gly Ser Thr
1               5

<210> SEQ ID NO 5
<211> LENGTH: 22
<212> TYPE: PRT
<213> ORGANISM: Homo sapiens

<400> SEQUENCE: 5

Ala Thr Asn Pro Thr Thr Val Phe Gly Val Val Thr Pro Asp Tyr Tyr
1               5                   10                  15

Tyr Tyr Pro Met Glu Val
            20

<210> SEQ ID NO 6
<211> LENGTH: 25
<212> TYPE: PRT
<213> ORGANISM: Homo sapiens

<400> SEQUENCE: 6

Gln Met Gln Leu Val Gln Ser Gly Pro Glu Gly Lys Lys Pro Gly Thr
1               5                   10                  15

Ser Val Lys Val Ser Cys Lys Ala Ser
            20                  25
```

```
<210> SEQ ID NO 7
<211> LENGTH: 17
<212> TYPE: PRT
<213> ORGANISM: Homo sapiens

<400> SEQUENCE: 7

Met Gln Trp Val Arg Gln Ala Pro Gly Gln Arg Leu Glu Trp Ile Gly
1               5                   10                  15

Trp

<210> SEQ ID NO 8
<211> LENGTH: 38
<212> TYPE: PRT
<213> ORGANISM: Homo sapiens

<400> SEQUENCE: 8

Lys Tyr Ser Gln Asn Phe Gln Glu Arg Val Thr Phe Ser Arg Asp Met
1               5                   10                  15

Ser Thr Ser Thr Ala Tyr Met Glu Leu Ser Ser Leu Arg Ser Glu Asp
            20                  25                  30

Thr Ala Val Tyr Tyr Cys
        35

<210> SEQ ID NO 9
<211> LENGTH: 11
<212> TYPE: PRT
<213> ORGANISM: Homo sapiens

<400> SEQUENCE: 9

Trp Gly Gln Gly Thr Thr Val Thr Val Ser Ser
1               5                   10

<210> SEQ ID NO 10
<211> LENGTH: 8
<212> TYPE: PRT
<213> ORGANISM: Homo sapiens

<400> SEQUENCE: 10

Asn Ser Asn Ile Gly Ser Asn Phe
1               5

<210> SEQ ID NO 11
<211> LENGTH: 11
<212> TYPE: PRT
<213> ORGANISM: Homo sapiens

<400> SEQUENCE: 11

Ala Val Trp Asp Asp Thr Leu Arg Val Trp Val
1               5                   10

<210> SEQ ID NO 12
<211> LENGTH: 25
<212> TYPE: PRT
<213> ORGANISM: Homo sapiens

<400> SEQUENCE: 12

Gln Ser Val Leu Thr Gln Pro Pro Ser Ala Ser Gly Thr Pro Gly Gln
1               5                   10                  15

Arg Val Ala Ile Ser Cys Ser Gly Gly
            20                  25

<210> SEQ ID NO 13
<211> LENGTH: 17
```

-continued

```
<212> TYPE: PRT
<213> ORGANISM: Homo sapiens

<400> SEQUENCE: 13

Val Tyr Trp Tyr Gln His Pro Pro Gly Thr Ala Pro Lys Leu Leu Ile
1               5                   10                  15

Phe

<210> SEQ ID NO 14
<211> LENGTH: 36
<212> TYPE: PRT
<213> ORGANISM: Homo sapiens

<400> SEQUENCE: 14

Gln Arg Pro Ser Gly Val Pro Asp Arg Phe Ser Gly Ser Lys Ser Gly
1               5                   10                  15

Thr Ser Ala Ser Leu Ala Val Ser Gly Leu Arg Thr Glu Asp Glu Ala
            20                  25                  30

Asp Tyr Phe Cys
        35

<210> SEQ ID NO 15
<211> LENGTH: 10
<212> TYPE: PRT
<213> ORGANISM: Homo sapiens

<400> SEQUENCE: 15

Phe Gly Gly Gly Thr Lys Leu Thr Val Leu
1               5                   10
```

FLAVIVIRUS CROSS NEUTRALIZING ANTIBODY AND PHARMACEUTICAL COMPOSITION

CROSS REFERENCE TO RELATED APPLICATIONS

This application is a National Stage of International Application No. PCT/JP2021/004022 filed Feb. 4, 2021, claiming priority based on Japanese Patent Application No. 2020-026736 filed Feb. 20, 2020.

TECHNICAL FIELD

The present invention relates to a flavivirus cross neutralizing antibody and a pharmaceutical composition containing the flavivirus cross neutralizing antibody as an active ingredient.

BACKGROUND ART

The genus Flavivirus of the family Flaviviridae includes many pathogens that cause infectious diseases that pose public health problems worldwide such as Zika virus, Japanese encephalitis virus, dengue virus, and west Nile virus.

The flavivirus is a spherical particle having a diameter of 50 to 60 nm in which nucleocapsid composed of C protein and genomic RNA is covered with an envelope derived from host endoplasmic reticulum membrane (NPL 1). There are 70 or more types of flaviviruses, most of which are transmitted via haematophagous arthropods.

The flavivirus genome is a positive-chain RNA with a total length of about 11 kb, and has a cap structure at the 5' end, but does not have a poly-A structure at the 3' end. On this genome, there is one reading frame, which encodes three structural proteins (C, prM, and E) and seven non-structural proteins (NS1, NS2A, NS2B, NS3, NS4A, NS4B, and NS5).

Some flavivirus infections become very severe, and the involvement of antibody-dependent enhancement (ADE) in the aggravation mechanism is strongly suggested. For example, if an existing anti-DENV antibody cross-bindings to a different type of DENV, the infection becomes very severe (NPLs 2, 3, and 4).

PTL 1 describes a flavivirus neutralizing antibody derived from mAb11 that recognizes the West Nile virus E protein and cross-reacts with members of the family Flavivirus including dengue virus.

CITATION LIST

Patent Literature

[PTL 1] Japanese Unexamined Patent Application Publication No. 2019-54796

Non Patent Literature

[NPL 1] Gubler D J, Kuno G, Markoff L: Flaviviruses. In: Fields virology (Fifth edition). Knipe D M, Howley P M (Ed), Lippincott-Raven, Philadelphia, PA, 1153-252, 2007.
[NPL 2] Brandt W E, McCown J M, Gentry M K, Russell P K. Infection enhancement of dengue type 2 virus in the U-937 human monocyte cell line by antibodies to flavivirus cross-reactive determinants. Infect. Immun. 36: 1036-41, 1982.

[NPL 3] Halstead S B, O'Rourke E J. Dengue viruses and mononuclear phagocytes. I. Infection enhancement by non-neutralizing antibody. J. Exp. Med. 146: 201-17, 1977.
[NPL 4] Halstead S B, Venkateshan C N, Gentry M K, Larsen L K. Heterogeneity of infection enhancement of dengue 2 strains by monoclonal antibodies. J. Immunol. 132: 1529-32, 1984.

SUMMARY OF INVENTION

Technical Problem

However, although the aforementioned flavivirus neutralizing antibody is excellent in ability to control infection, the antibody-dependent enhancement (ADE) thereof is not sufficiently suppressed.

The present invention has an object to provide a flavivirus cross neutralizing antibody which has an excellent ability to control infection with suppressed ADE.

Solution to Problem

A flavivirus cross neutralizing antibody according to the present invention is a flavivirus cross neutralizing antibody that specifically binds to domains of E protein of flavivirus and thereby has an ability to control infection with at least two viruses included in the flavivirus, characterized in that the domains of E protein include a plurality of domains including domain III.

Advantageous Effects of Invention

According to the present invention, it is possible to obtain a flavivirus cross neutralizing antibody which has an excellent ability to control infection with suppressed ADE.

BRIEF DESCRIPTION OF DRAWINGS

FIG. 1 includes diagrams presenting measurement results of antibody-dependent enhancement.

FIG. 2 is a diagram presenting in vivo test results of an ability to prevent infection of an antibody according to the present invention.

DESCRIPTION OF EMBODIMENTS

Hereinafter, embodiments of the present invention will be described specifically in reference to the accompanying drawings. The embodiments are merely for facilitating understanding of the principle of the present invention. The scope of the present invention should not be limited to the following embodiments and may also include other embodiments in which configurations of the following embodiments are altered as appropriate by those skilled in the art.

The E protein of flavivirus is the most important protein on viral particles, forming homodimers on mature particles, and forming homotrimers due to a structural change caused when exposed to low pH in endosomes after infection.

In the intracellular immature particles, 180 prM-E heterodimers are present on the envelope, and three of the heterodimers form one spike. When the particles are in this structure, the prM protein obscures and does not expose the fusion loop on the E protein to be involved in membrane fusion. After that, when the particles reach the trans-Golgi network through the intracellular endocrine pathway and are exposed to low pH, they undergo a structural change and have a smooth surface structure. When prM is cleaved by the Golgi apparatus Flynn to become M protein, the prM-E heterodimers are dissociated to form 90 E-E homodimers, resulting in mature particles. After infection, when exposed to low pH in endosomes, the E protein undergoes surface structure rearrangement, forms spike-form E-E-E homotrimers, and causes membrane fusion with endosome membrane.

The E protein include three domains, and the fusion loop is present in domain II whereas the receptor binding region is present in domain III. The present inventor has found as a new finding that an antibody that binds not only to domain III of E protein but also to another domain has an ability to control infection with a plurality of viruses and the ADE therein can be suppressed, and has completed, based on this fact, a flavivirus cross neutralizing antibody (in some cases simply referred to as antibody) according to the present invention.

The antibody according to the present invention may be, for example, human IgG1, IgG2, IgG3, IgG4, or a variant thereof, or rat IgM, IgG1, IgG2a, IgG2b, IgG3, IgA, IgD, IgE, or a variant thereof. Any heavy chain may be paired with a κ or λ type light chain. The antibody contains a Fab fragment, a F(ab')2 fragment, or an Fv fragment.

The sequence of a heavy chain variable region of the antibody according to the present invention is as follows.

(SEQ ID NO: 1)
QMQLVQSGPEGKKPGTSVKVSCKASGFTFSRTTMQWVRQAPGQRLEWIGW

IVIGTGSTKYSQNFQERVTFSRDMSTSTAYMELSSLRSEDTAVYYCATNP

TTVFGVVTPDYYYYPMEVWGQGTTVTVSS

The CDRs of the heavy chain variable region are defined by GFTFSRTT (CDR1) (SEQ ID NO: 3), IVIGTGST (CDR2) (SEQ ID NO: 4) and ATNPTTVFGVVTPDYYYYPMEV (CDR3) (SEQ ID NO: 5).

The FRs of the heavy chain variable region are defined by QMQLVQSGPEGKKPGTSVKVSCKAS (FR1) (SEQ ID NO: 6), MQWVRQAPGQRLEWIGW FR2) (SEQ ID NO: 7), KYSQNFQER VTFSRDMSTSTAYMELSSLRSED-TAVYYC (FR3) (SEQ ID NO: 8), and WGQGTTVTVSS (FR4) (SEQ ID NO: 9).

The sequence of a light chain variable region of the antibody according to the present invention is as follows.

(SEQ ID NO: 2)
QSVLTQPPSASGTPGQRVAISCSGGNSNIGSNFVYWYQHPPGTAPKLLIF

RNDQRPSGVPDRFSGSKSGTSASLAVSGLRTEDEADYFCAVWDDTLRVWV

FGGGTKLTVL

The CDRs of the light chain variable region are defined by NSNIGSNF (CDR1) (SEQ ID NO: 10), RND (CDR2), and AVWDDTLRVWV (CDR3) (SEQ ID NO: 11).

The FRs of the light chain variable region are defined by QSVLTQPPSASGTPGQRVAISCSGG (FR1) (SEQ ID NO: 12), VYWYQHPPGTAPKLLIF (FR2) (SEQ ID NO: 13), QRPSGVPDRFSGSKSGTSASLAVSGLRTEDEADYFC (FR3) (SEQ ID NO: 14), and FGGGTKLTVL (FR4) (SEQ ID NO: 15).

The ADE is considered to be caused mainly by a phenomenon in which an antibody cross-links cells and a virus via the Fcγ receptor IIa (FcγRIIa) and the adsorption efficiency of the virus increases. For this reason, the F(ab')2 antibody from which the Fc region of the antibody, which is considered to be the main factor of ADE, has been removed is advantageous in that the ADE can be suppressed while the neutralizing ability is maintained.

The antibody according to the present invention can also include an antibody derivative modified or complexed by a covalent bond between any kind of molecule and the antibody. Examples of such antibody derivative include: derivatives by acetylation, glycosylation, amidation, PEGylation, phosphorylation, and known protecting group/blocking group; and antibodies modified by proteolytic cleavage, or binding to intracellular ligands or another protein or low molecular weight compound.

A method for obtaining the antibody according to the present invention is not particularly limited. An antibody desired to be obtained may be obtained by culturing a hybridoma that produces the antibody and purifying the antibody from the obtained culture supernatant by using a conventional method. A method for harvesting the antibody from the hybridoma obtained is not particularly limited. For example, it is possible to use a normal ascites formation method or cell culture method. In an alternative method, an antibody desired to be obtained can be also produced in such a way that a gene encoding the antibody, more specifically, a gene encoding a heavy chain and a light chain of an immunoglobulin is obtained from a hybridoma that produces the antibody, and a vector for expressing the gene is prepared and is introduced into host cells (such as mammalian cells, insect cells, or microorganisms).

(Pharmaceutical Composition)

A pharmaceutical composition according to the present invention contains a flavivirus cross neutralizing antibody according to the present invention as an active ingredient. The pharmaceutical composition according to the present invention is administered by either oral or parenteral administration. The parenteral administration is a particularly preferable administration method, and specifically includes injection administration, nasal administration, transpulmonary administration, transdermal administration, and the like. As an example of the injection administration, the pharmaceutical composition is administered systemically or locally by intravenous injection, intramuscular injection, intraperitoneal injection, subcutaneous injection, or the like.

The administration method is not particularly limited and may be selected as appropriate depending on, for example, the age and symptoms of a patient. Regarding a dose, for example, a dose per kg body weight per administration is selected in the range of 0.0001 mg to 1000 mg. Alternatively, for example, a dose per patient is selected in the range of 0.001 to 100000 mg/body. Regarding an administration timing, the pharmaceutical composition according to the embodiment may be administered at any timing regardless of before or after the onset of clinical symptoms of a disease.

The flavivirus cross neutralizing antibody according to the present invention is formulated according to a conventional method so as to contain a pharmaceutically acceptable carrier and additives together, thereby being formed as a pharmaceutical composition.

In the case of an orally administered preparation, the flavivirus cross neutralizing antibody is formulated in the form of tablets, granules, fine granules, capsules or the like, containing a dispersant and/or a dissolution improver together with a preparation carrier. As the preparation carrier, it is possible to use excipients, binders, disintegrators, lubricants, plasticizers, and the like. As the excipients, it is possible to use, for example, white soft sugar, sodium chloride, mannitol, lactose, glucose, starch, calcium carbonate, and the like. As the binders, it is possible to use, for example, water, ethanol, propanol, glucose solution, starch solution, gelatin solution, sodium carboxymethyl cellulose, methyl cellulose, and the like. As the disintegrators, it is possible to use, for example, carboxymethyl cellulose calcium, dry starch, sodium hydrogen carbonate, calcium hydrogen carbonate, and the like. As the lubricants, it is possible to use, for example, purified talc, stearate, borate powder, polyethylene glycol, and the like. As the plasticizers, it is possible to use, for example, glycerin fatty acid ester, castor oil, and the like. As the dispersants and/or the dissolution improvers, it is possible to use, for example, water-soluble polymers, surfactants, and the like. As the water-soluble polymers, it is possible to use, for example, hydroxypropyl cellulose, polyvinyl alcohol, polyvinylpyrrolidone, polyacrylic acid, and the like. As the surfactants, it is possible to use, for example, alkyl sulfate such as sodium lauryl sulfate and magnesium lauryl sulfate.

An oral liquid preparation is prepared by mixing a sweetener (for example, sucrose), a preservative (for example, methylparaben or propylparaben), a colorant, a flavor, and the like.

An injection preparation among parenteral preparations is prepared, for example, in the form of a liquid preparation, an emulsion, or a suspension, and is made isotonic with respect to blood. The preparation in the form of a liquid, an emulsion, or a suspension is prepared by using, for example, an aqueous medium, ethyl alcohol, propylene glycol, or the like. As the aqueous medium, there is water or a medium containing water. As the water, sterile water is used. Examples of the medium containing water include saline, PBS (phosphate buffered saline), Ringer's solution containing lactic acid, and the like.

The injection preparation may use additives which are usually used in this technical field. Examples of the additives include tonicity agents, stabilizers, buffers, preservatives, chelating agents, antioxidants, solubilizing agents, and the like. Examples of the tonicity agents include saccharides such as glucose, sorbitol, and mannitol, sodium chloride, glycerin, propylene glycol, polyethylene glycol, and the like. Examples of the stabilizers include sodium sulfite and the like. Examples of the buffers include borate buffer, phosphate buffer, citrate buffe, tartrate buffer, acetate buffer, and the like. Examples of the preservatives include para-hydroxybenzoate, benzyl alcohol, chlorocresol, phenethyl alcohol, benzethonium chloride, and the like. Examples of the chelating agents include sodium edetate, sodium citrate, and the like. Examples of the antioxidants include sodium sulfite, sodium hydrogen sulfite, sodium ascorbate, sodium thiosulfate, and the like. Examples of the solubilizing agents include dextran, polyvinylpyrrolidone, sodium benzoate, ethylenediamine, salicylic acid amide, nicotinic acid amide, polyoxyethylene hydrogenated castor oil derivative, and the like.

The pharmaceutical composition according to the present invention contains the flavivirus cross neutralizing antibody according to the present invention as the active ingredient and is effective against viruses in the genus Flavivirus of the family Flaviviridae. For example, the pharmaceutical composition is effective against Zika virus, dengue virus, Japanese encephalitis virus, west Nile virus, yellow fever virus, Murray Valley encephalitis virus, St. Louis encephalitis virus, tick-borne encephalitis virus (TBEV), and the like.

EXAMPLE

1. Preparation of Monoclonal Antibody as Candidate Target

IgG-positive memory B cells binding to flavivirus E protein were isolated from among human peripheral blood cells (CD19-positive IgG-positive CD38-negative cells were gated from among CD2-negative CD4-negative IgD-negative living cells) by flow cytometry. The isolated cells were dispensed, on a one-cell per well basis, into 96 wells where MS40L feeder cells (cells already reported in Immunity. 2016 Mar. 15; 44(3): 542-552. doi: 10.1016/j.immuni.2016.02.010. Epub 2016 Mar. 3) were cultured in a monolayer and human IL-2 (50 ng/ml). IL-4 (10 ng/ml), IL-21 (10 ng/ml), and BAFF (10 ng/ml) were contained, followed by culturing for 25 days. After that, the culture supernatants of multiple wells containing human IgG monoclonal antibody were collected.

2. Selection of Antibody ZDJ01

The multiple culture supernatants containing the human IgG monoclonal antibody were subjected to a test using single-round infectious particles described below, and ZDJ01, which is an antibody according to this Example, was selected.

That is, a neutralization test using the single-round infectious particles was as follows. The single-round infectious particles (SRIPs) were produced from 10 types of flaviviruses: dengue virus types 1-4, Japanese encephalitis virus, west Nile virus, yellow fever virus, tick-borne encephalitis virus, and St. Louis encephalitis virus (the method is described in Matsuda M, Yamanaka A, Yato K, et al. High-throughput neutralization assay for multiple flaviviruses based on single-round infectious particles using dengue virus type 1 reporter replicon. Sci Rep 2018; 8:16624). Each type of single-round infectious particles was diluted such that 50 infectious particles were contained per well, followed by culturing together with the diluted human IgG monoclonal antibody (purified antibody or culture supernatant) over night at 4° C., and then the resultant particles were added to Vero cells cultured in a monolayer in a 96-well plate. After culturing for 6 hours at 37° C., the supernatant was removed and a new culture medium was added, followed by culturing for 3 days at 37° C. Then, the luciferase activity of each well was measured by the Nano-Glo luciferase assay system, and ZDJ01 was selected.

3. Isolation of Antibody ZDJ01

Cells were collected from the wells from which the culture supernatant of ZDJ01 was collected, and the antibody gene variable regions (IgVH, IgVL) were amplified by PCR and cloned into expression vectors (protocol described in Tiller T, Meffre E, Yurasov S, Tsuiji M, Nussenzweig M C, Wardemann H. Efficient generation of monoclonal antibodies from single human B cells by single cell RT-PCR and expression vector cloning. J Immunol Methods 2008; 329: 112-24). Gene transfer of the heavy and light chain expression vectors into 293-F cells was performed using the FreeStyle™ 293 Expression System (Thermo Fisher Scientific, USA). After 5 days, the culture supernatant was collected and the monoclonal IgG antibody was purified using a HiTrap protein G column (GE Healthcare).

The sequence of the heavy chain variable region of ZDJ01 was as follows.

(SEQ ID NO: 1)
QMQTVQSGPEGKKPGTSVKVSCKASGFTFSRTTMQWVRQAPGQRLEWIGW

IVIGTGSTKYSQNFQERVTFSRDMSTSTAYMELSSLRSEDTAVYYCATNP

TTVFGVVTPDYYYYPMEVWGQGTTVTVSS

The sequence of the light chain variable region of ZDJ01 was as follows.

(SEQ ID NO: 2)

QSVLTQPPSASGTPGQRVAISCSGGNSNIGSNFVYWYQHPPGTAPKLDIF

RNDQRPSGVPDRFSGSKSGTSASLAVSGLRTEDEADYFCAVWDDTLRVWV

FGGGTKLTVL

In addition, as shown in Table 1 below, the antibody ZDJ01 achieved high protective immunity against three viruses, for example, Zika virus (ZIKV), dengue virus type 1 (DENV1), and Japanese encephalitis virus (JEV), and the cross neutralization activity of the antibody ZDJ01 was excellent.

TABLE 1

| IC50 (ng/mL) | ZDJ01 | Z004 |
|---|---|---|
| ZIKV | 0.58 | 1.69 |
| DENV1 | 53.36 | 8.50 |
| DENV2 | 1.93 | >10000 |
| DENV3 | 13.49 | >10000 |
| DENV4 | 5.18 | >10000 |
| JEV | 19.58 | >10000 |
| SLEV | 16.33 | >10000 |
| WNV | 1.73 | >10000 |
| TBEV | 49.85 | >10000 |
| YFV | 0.95 | >10000 |

4. ADE Activity of Antibody ZDJ01

The neutralizing ability of an antibody is usually measured in cells without FcγR such as Vero cells using the plaque reduction method (PRNT method). In such a neutralization test method, only the neutralizing ability is measured and the neutralizing ability that reflects the infection enhancing effect is not measured. Therefore, the ADE activity of the antibody ZDJ01 was measured by the neutralization test using the above-mentioned single-round infectious particles (SRIPs) with its content changed from Vero cells to K562 cells that express the Fcg receptor. The presence or absence of ADE was determined based on the ratio of increased luciferase activity where ZDJ01 or Z004 IgG antibody was added, relative to the luciferase activity where no antibody was added set as 1. As shown in FIG. 1, the antibody ZDJ01 did not demonstrate increases unlike the antibody Z004, and therefore the antibody-dependent enhancement was determined as absent in the antibody ZDJ01.

From above, the antibody ZDJ01 was found to have high protective immunity against multiple viruses included in the flavivirus and not to cause antibody-dependent enhancement (ADE).

5. In Vivo Test

A group of ddY mice (4 week old females, 10 animals per group) was intraperitoneally administered with 0.2 mg of ZDJ01, Z004, or influenza IgG antibody (V15-5, negative control). One day after the antibody administration, the mice were intraperitoneally infected with 10 LD50 of Japanese encephalitis virus Beijing strain, and the survival rate for 21 days was observed. As shown in FIG. 2, the in vivo test demonstrated that the antibody ZDJ01 had a high protective immune ability against not only Zika virus but also Japanese encephalitis virus.

INDUSTRIAL APPLICABILITY

The present invention is usable for treatment of flavivirus infectious diseases.

The invention claimed is:

1. A flavivirus cross neutralizing antibody that specifically binds to E protein of flavivirus,
   wherein the flavivirus cross neutralizing antibody comprises:
   a heavy chain variable region comprising complementarity determining region 1 (CDR1) of GFTFSRTT (SEQ ID NO: 3), CDR2 of IVIGTGST (SEQ ID NO: 4), and CDR3 of ATNPTTVFGVVTPDYYYPMEV (SEQ ID NO: 5), and
   a light chain variable region comprising CDR1 of NSNIGSNF (SEQ ID NO: 10), CDR2 of RND, and CDR3 of AVWDDTLRVWV (SEQ ID NO: 11).

2. The flavivirus cross neutralizing antibody according to claim 1, which comprises a heavy chain variable region containing framework region 1 (FR1) of QMQLVQSG-PEGKKPGTSVKVSCKAS (SEQ ID NO: 6), FR2 of MQWVRQAPGQRLEWIGW (SEQ ID NO: 7), FR3 of KYSQNFQERVTFSRDMSTSTAYMELSSLRSED-TAVYYC (SEQ ID NO: 8), and FR4 of WGQGTTVTVSS (SEQ ID NO: 9).

3. The flavivirus cross neutralizing antibody according to claim 1, which comprises a light chain variable region containing framework region 1 (FR1) of QSVLTQPP-SASGTPGQRVAISCSGG (SEQ ID NO: 12), FR2 of VYWYQHPPGTAPKLLIF (SEQ ID NO: 13), FR3 of QRPSGVPDRFSGSKSGTSASLAVSGLRTEDEADYFC (SEQ ID NO: 14), and FR4 of FGGGTKLTVL (SEQ ID NO: 15).

4. The flavivirus cross neutralizing antibody according to claim 1, wherein
   a heavy chain variable region is QMQLVQSG-PEGKKPGTSVKVSCK-ASGFTFSRTTMQWVRQAPGQRLEWIG-WIVIGTGST KYSQNFQERVTFSRDMSTSTAYMELSSLRSED-TAVYYCATNPTTVFGVVTPDYYYPM EVWGQGTTVTVSS (SEQ ID NO: 1), and
   a light chain variable region is QSVLTQPP-SASGTPGQRVAISCSGGNSNIG-SNFVYWYQHPPGTAPKLLIFRNDQRPSGVP DRFSGSKSGTSASLAVSGLRTEDEAD-YFCAVWDDTLRVWVFGGGTKLTVL (SEQ ID NO: 2).

5. The flavivirus cross neutralizing antibody according to claim 1, wherein the flavivirus is dengue virus types 1-4, Japanese encephalitis virus, west Nile virus, yellow fever virus, tick-borne encephalitis virus, or St. Louis encephalitis virus.

6. A pharmaceutical composition comprising the flavivirus cross neutralizing antibody according to claim 1.

* * * * *